United States Patent [19]

Bitha et al.

[11] Patent Number: 4,870,070

[45] Date of Patent: Sep. 26, 1989

[54] WATER SOLUBLE PLATINUM COMPLEXES OF NOVEL MALONATE DERIVATIVES

[75] Inventors: Panayota Bitha, Nanuet; Joseph J. Hlavka, Tuxedo Park; Yang-I Lin, Tappan, all of N.Y.

[73] Assignee: American Cyanamid Company, Stamford, Conn.

[21] Appl. No.: 83,325

[22] Filed: Aug. 10, 1987

[51] Int. Cl.$^4$ .................... A61K 31/555; A61K 31/28
[52] U.S. Cl. .................... 514/184; 514/492; 549/3; 549/208; 549/211; 556/137
[58] Field of Search .......... 549/3, 208, 211; 556/137; 514/184, 492

[56] References Cited

U.S. PATENT DOCUMENTS

| | | | |
|---|---|---|---|
| 4,410,544 | 10/1983 | Berg et al. | 556/137 X |
| 4,562,275 | 12/1985 | Speer et al. | 556/137 X |
| 4,614,811 | 9/1986 | Gandolfi | 556/137 |
| 4,665,210 | 5/1987 | Bitha et al. | 556/137 |
| 4,675,336 | 6/1987 | Bitha et al. | 514/492 |
| 4,737,589 | 4/1988 | Nowatari et al. | 556/137 |
| 4,748,254 | 5/1988 | Cheltson-Bebutov et al. | 556/137 X |

FOREIGN PATENT DOCUMENTS 60-248779  5/1987  Japan ............... 556/137 X

OTHER PUBLICATIONS

Chemical Abstracts 107:125930n (1987).
Chemical Abstracts 107:189634b (1987).
Chemical Abstracts 108:215337z (1988).

*Primary Examiner*—H. M. S. Sneed
*Assistant Examiner*—George R. Fourson
*Attorney, Agent, or Firm*—H. G. Jackson

[57] ABSTRACT

This disclosure describes water soluble platinum complexes of novel malonate derivatives which possess the property of inhibiting the growth of tumors in mammals.

8 Claims, No Drawings

WATER SOLUBLE PLATINUM COMPLEXES OF NOVEL MALONATE DERIVATIVES

This invention is concerned with new organic compounds of the formulae:

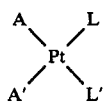

wherein A and A' taken together are:

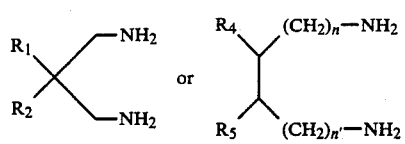

where $R_1$ and $R_2$ in formula (a) may be the same or different and may be selected from hydrogen, $HO(CH_2)_m-$ where m is an integer from 1 to 3, and lower alkyl having from one to three carbon atoms, or $R_1$ and $R_2$ taken together may be $-(CH_2)_{m'}-B-(CH_2)_{m''}-$ where B is selected from oxygen, $-SO_2-$, $-CH_2-$ and $N-R_3$ where $R_3$ is lower alkyl having from one to three carbon atoms and where m' and m" may be an integer from 0-4; $R_1$ and $R_2$ taken together may also be

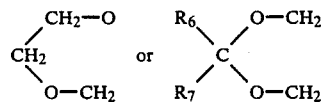

where $R_6$ and $R_7$ may both be hydrogen or lower alkyl, having from one to three carbon atoms; wherein the formula (b) n and n' may be zero or one; $R_4$ and $R_5$ may both be $HO(CH_2)_m-$ where m is an integer from 1 to 3, or $R_4$ and $R_5$ taken together may be $-(CH_2)_p-D-(CH_2)_{p'}-$, where D is selected from oxygen, $-CH_2-$ and

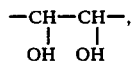

where p and p' may be an integer from 0-4; $R_4$ and $R_5$ taken together may also be

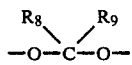

where $R_8$ and $R_9$ may be hydrogen or lower alkyl having from one to three carbon atoms; and wherein L and L' taken together is a dibasic carboxylate of:

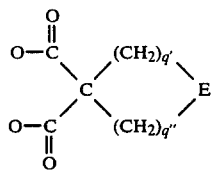

where E is selected from oxygen, $-SO_2-$ and $N-R_{10}$ where $R_{10}$ is lower alkyl having from one to three carbon atoms and where q' and q" may be an integer from 0-4; L and L' taken together may also be

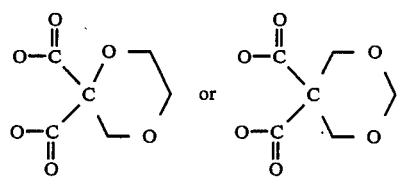

or A and A' may both be $NH_3$.

DETAILED DESCRIPTION OF THE INVENTION

The compounds of this invention may be prepared according to the following reaction schemes.

Flowchart I

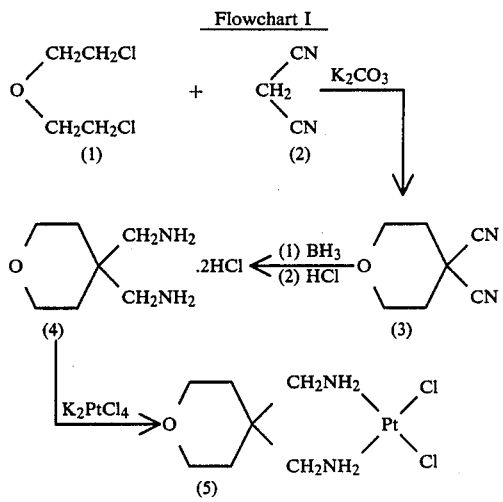

According to Flowchart I dichloroethyl ether (1) is reacted with malononitrile (2) in the presence of potassium carbonate in acetonitrile at reflux, giving tetrahydro-4H-pyran-4,4-dicarbonitrile (3) which is then reduced with 1N borane in tetrahydrofuran followed by treatment with hydrochloric acid, giving tetrahydro-4H-pyran-4,4-dimethanamine dihydrochloride (4) which is then reacted with a mixture of sodium acetate and potassium tetrachloroplatinate in water, giving the intermediate compound dichloro(tetrahydro-4H-pyran-4,4-dimethanamine-N,N')platinum (5).

Flowchart II

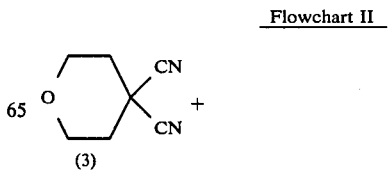

-continued
Flowchart II

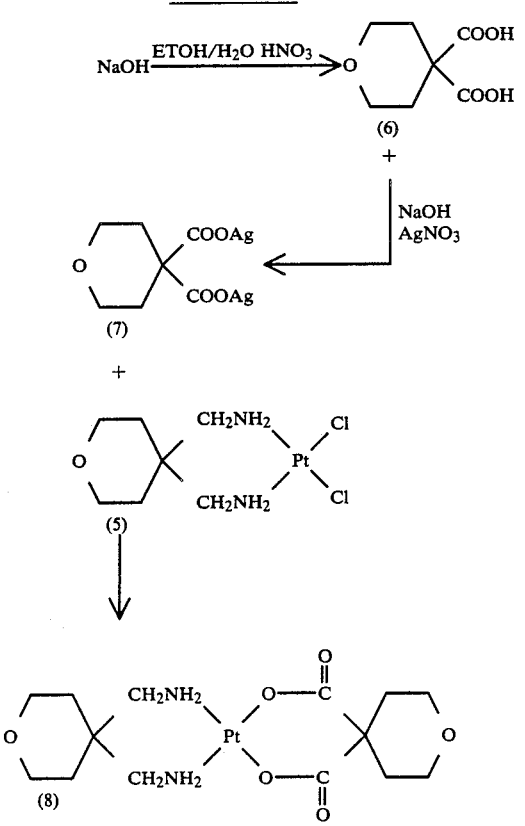

In Flowchart II tetrahydro-4H-pyran-4,4-dicarbonitrile (3) is dissolved in a mixture of ethanol, 10N sodium hydroxide and water and is heated at reflux. Evaporation and treatment of the residue with nitric acid gives tetrahydro-4H-pyran-4,4-dicarboxylic acid (6). Treatment of the sodium salt of (6) with silver nitrate in water gives the tetrahydro-4H-pyran-4,4-dicarboxylic acid, disilver salt (7). When the salt (7) is stirred in water with the intermediate (5) the product [tetrahydro-4H-pyran-4,4-dicarboxylato-(2-)-O,O'](tetrahydro-4H-pyran-4,4-dimethanamine-N,N')platinum (8) is obtained.

Flowchart III

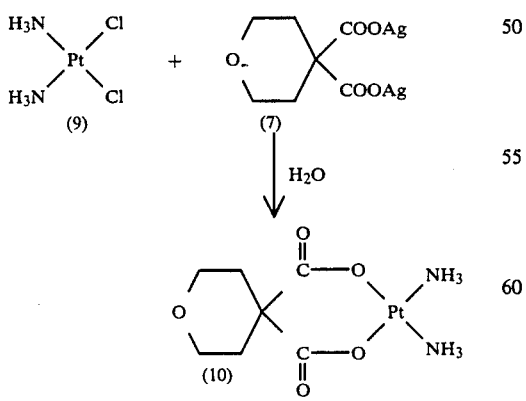

In Flowchart III the compound diammine[tetrahydro-4H-pyran-4,4-dicarboxylato-(2-)-O,O']platinum (10) is prepared by reacting tetrahydro-4H-pyran-4,4-dicarboxylic acid, disilver salt (7) with cis diamminedichloroplatinum (9).

In accordance with Flowchart IV (-1-R,R-1,2-diaminocyclohexane (11) is reacted with potassium tetrachloroplatinate in water giving trans-1,2-cyclohexanediamine, compound with platinum chloride (12). Compound (12) is reacted with tetrahydro-4H-pyran-4,4-dicarboxylic acid, disilver salt (7) in water. The product trans-(-)-(1,2-cyclohexanediamine-N,N')[tetrahydro-4H-pyran-4,4-dicarboxylato-(2-)-O,O']-platinum (13) is obtained by evaporating the filtrate.

Flowchart IV

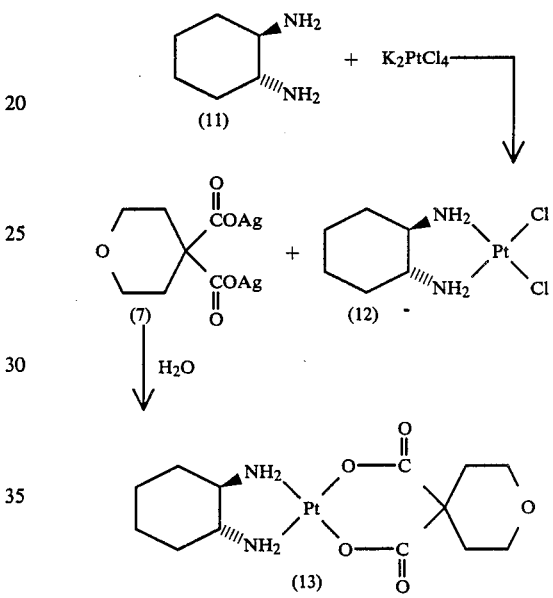

In Flowchart V [2,2-bis(aminomethyl)-1,3-propanediol-N,N']dichloroplatinum (14) is reacted with tetrahydro-4H-pyran-4,4-dicarboxylic acid, disilver salt (7) in water. The silver chloride is removed by filtration. The filtrate is concentrated giving the product [2,2-bis(aminomethyl)-1,3-propanediol-N,N'][tetrahydro-4H-pyran-4,4-dicarboxylato-(2-)-O,O']platinum (15).

Flowchart V

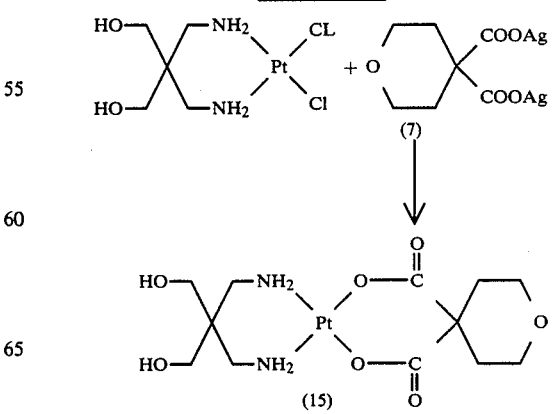

Flowchart VI

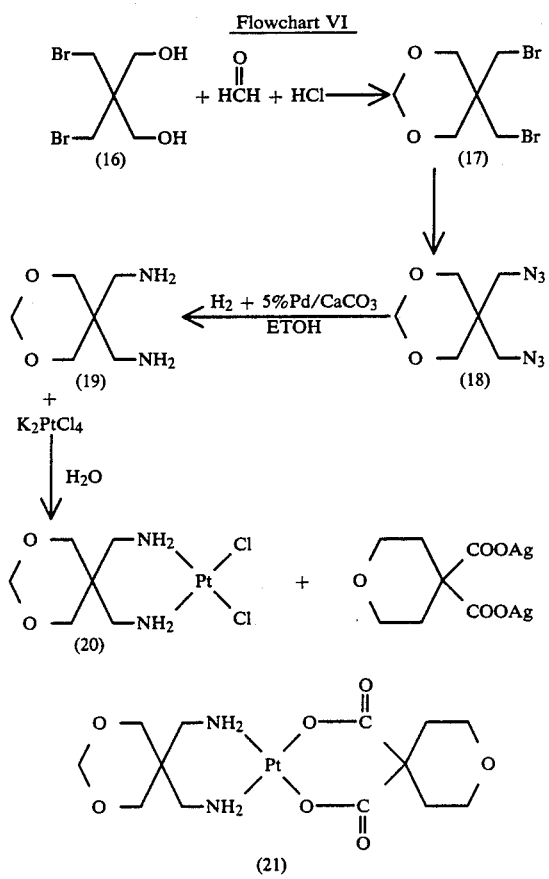

In accordance with Flowchart VI 2,2-bis(bromomethyl)-1,3-propanediol (16) is reacted with formaldehyde/hydrochloric acid by heating at 50° C., then separating 5,5-bis(bromomethyl)-1,3-dioxane (17) as an oil. The oil (17) in N,N-dimethylformamide is reacted with sodium azide at 130° C. The mixture is filtered and the filtrate is evaporated to an oil which is extracted from water with ether giving 5,5-bis(azidomethyl)-1,3-dioxane (18). The product (18) in ethanol is hydrogenated with 5% palladium catalyst on calcium carbonate to give 5,5-dimethanamine-1,3-dioxane (19) which is then reacted with potassium tetrachloroplatinate in water, giving the compound dichloro(1,3-dioxane-5,5-dimethanamine-N,N')platinum (20). A suspension of (20) and tetrahydro-4H-pyran-4,4-dicarboxylic acid, disilver-(1+)salt (7) in water is stirred in the dark and filtered. The filtrate is evaporated giving the product (1,3-dioxane-4,4-dimethanamine-N,N')[tetrahydro-4H-pyran-4,4-dicarboxylato-(2-)-O,O']platinum (21). 4,4-dimethanamine-N,N')[tetrahydro-4H-pyran-4,4-dicarboxylato-(2-)-O,O']platinum (21).

The novel complexed compounds of this invention possess the property of inhibiting the growth of tumors in mammals as estabished by the following tests.

Lymphocytic Leukemia P388 Test

The animals used were BDF/1 mice all of one sex per test, weighing a minimum of 18 g and all within a 3 g weight range. There were 5 or 6 animals per test group. The tumor transplant was by intraperitoneal injection of 0.5 ml of diluted ascitic fluid containing $10^6$ cells of lymphocytic leukemia P388. The test commpounds were administered intraperitoneally on days 1, 5 and 9 relative to tumor inoculation, at various doses. The animals were weighed and the survivors recorded on a regular basis for 30 days. The median survival time and the ratio for treated (T)/control (C) animals were calculated. The positive control compound was Cisplatin. The results of this test with representative compounds of this invention appear in Table I.

TABLE I

Lymphocytic Leukemia P388 Test

| Compound | Dose (mg/kg) | Median Survival (Days) | T/C × 100 (%) |
|---|---|---|---|
| [Tetrahydro-4H—pyran-4,4-dicarboxylato(2—)-0,0']-(tetrahydro-4H—pyran-4,4-dimethanamine-N,N')platinum | 100 | 24 | 200 |
| | 50 | 23.5 | 196 |
| | 25 | 19.5 | 163 |
| | 12.5 | 17.5 | 146 |
| | 6.2 | 14 | 117 |
| | 3.1 | 13.5 | 113 |
| | 1.5 | 13 | 108 |
| Control | — | 12 | — |
| Cisplatin | 4 | 29.5 | 246 |
| | 2 | 25 | 208 |
| | 1 | 19.5 | 163 |
| Diammine[tetrahydro-4H—pyran-4,4-dicarboxylato(2—)-0,0']platinum | 100 | 18.5 | 154 |
| | 50 | 25.5 | 213 |
| | 25 | 21.5 | 179 |
| | 12.5 | 15.5 | 129 |
| | 4.2 | 15 | 125 |
| | 3.1 | 14 | 117 |
| | 1.5 | 13 | 108 |
| Control | — | 12 | — |
| Cisplatin | 4 | 29.5 | 246 |
| | 2 | 25 | 208 |
| | 1 | 19.5 | 163 |
| trans-(—)-(1,2-Clyclohexane-diamine-N,N')[tetrahydro-4H—pyran-4,4-dicarboxylato(2—)-0,0']platinum | 100 | 21 | 175 |
| | 50 | 22 | 183 |
| | 25 | 20 | 167 |
| | 12.5 | 20.5 | 171 |
| | 6.2 | 18 | 150 |
| | 3.1 | 15 | 125 |
| | 1.5 | 14 | 117 |
| Control | — | 12 | — |
| Cisplatin | 4 | 29.5 | 246 |
| | 2 | 25 | 208 |
| | 1 | 19.5 | 163 |
| [2,2-Bis(aminomethyl)-1,3-propanediol-N,N'][tetrahydro-4H—pyran-4,4-dicarboxylato(2—)-0,0']platinum | 100 | 5 | 50 |
| | 50 | 6 | 60 |
| | 25 | 9 | 90 |
| | 12.5 | 27.5 | 275 |
| | 6.2 | 25 | 250 |
| | 3.1 | 21 | 210 |
| Control | — | 10 | — |
| Cisplatin | 4 | >30 | >300 |
| | 2 | 24.5 | 245 |
| | 1 | 18.5 | 185 |
| (1,3-Dioxane-4,4-dimethanamine-N,N')[tetrahydro-4H—pyran-4,4-dicarboxylato(2—)-0,0']platinum | 100 | 26.5 | 265 |
| | 50 | 22.5 | 225 |
| | 25 | 20 | 200 |
| | 12.5 | 16 | 160 |
| | 6.2 | 14 | 140 |
| | 3.1 | 13 | 130 |
| Control | — | 10 | — |
| Cisplatin | 4 | >30 | >300 |
| | 2 | 24.5 | 245 |
| | 1 | 18.5 | 185 |

Lymphocytic Leukemia L1210 Test

The animals used were $BDF_1$ or $CD_2F_1$ mice, all of one sex, weighing a minimum of 17 g and all within a 3 g weight range. There were 6 mice per test group and 18 in control groups. The tumor transplant was by intraperitoneal injection of 0.5 ml of lymphocytic leukemia L1210 at a concentration of $10^5$ cells per mouse. The test compounds were administered on days 1, 5 and 9 (relative to tumor inoculation) at various doses. The mice were weighed and survivors recorded on a regular basis for 30 days. The mean survival time and the ratio of survival time for treated (T)/control(C) animals were calculated. The positive control compound was Cisplatin given intraperitoneally at the indicated doses. The results of this test on representative compounds of this invention appear in Table II.

TABLE II

Lymphocytic Leukemia L1210 Test

| Compound | Dose (mg/kg) | Median Survival (Days) | T/C × 100 (%) |
|---|---|---|---|
| [Tetrahydro-4H—pyran-4,4-dicarboxylato(2−)-0,0'](tetrahydro-4H—pyran-4,4-dimethanamine-N,N')platinum | 100 | 11 | 138 |
| | 50 | 25 | 313 |
| | 25 | 12.5 | 156 |
| | 12.5 | 9.5 | 119 |
| | 6.2 | 9 | 113 |
| Control | — | 8 | — |
| Cisplatin | 4 | 18.5 | 231 |
| | 2 | 12.5 | 156 |
| | 1 | 10.5 | 131 |
| Diammine[tetrahydro-4H—pyran-4,4-dicarboxylato(2−)0,0']-platinum | 50 | 11 | 138 |
| | 25 | 10 | 125 |
| | 12.5 | 9 | 113 |
| | 6.2 | 9 | 113 |
| | 3.1 | 9 | 113 |
| Control | — | 8 | — |
| Cisplatin | 4 | 18.5 | 231 |
| | 2 | 12.5 | 156 |
| | 1 | 10.5 | 131 |
| trans-(−)-(1,2-Cyclohexanediamine-N,N')[tetrahydro-4H—pyran-4,4-dicarboxylato(2−)-0,0']platinum | 100 | 15.5 | 194 |
| | 50 | 14.5 | 181 |
| | 25 | 15.5 | 194 |
| | 12.5 | 14.5 | 181 |
| | 6.2 | 11 | 138 |
| Control | — | 8 | — |
| Cisplatin | 4 | 18.5 | 231 |
| | 2 | 12.5 | 156 |
| | 1 | 10.5 | 131 |

The invention includes the novel compositions of matter and the method of inducing the regression and/or palliation of leukemia and related cancers in mammals using the novel compounds of this invention when administered in amounts ranging from about 1 mg to about 1.2 g per square meter of body surface area per day. The interrelationship of dosages for animals of various sizes and species and humans (based on mg/m$^2$ of surface area) is described by Freireich, E. J., et al., Quantitative Comparison of Toxicity of Anticancer Agents in Mouse, Rat, Hamster, Dog, Monkey and Man, Cancer Chemother. Rep., 50, No. 4, 219–244, May 1966. A preferred dosage regimen for optimum results would be from about 3 mg/m$^2$/day to about 200 mg/m$^2$/day and such dosage units are employed that a total of from about 5 mg to about 360 mg of the active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The active compound may be administered by the intravenous, intramuscular, or subcutaneous routes.

The active compunds may be administered parenterally. Solutions or dispersions of the active compound can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases it will be preferable to include isotonic agents, for example sugars or sodium chloride. Prolonged absorption of the injectable compositions can be obtained by the use in the compositions of agents which delay absorption, for example aluminum monostearate and gelatin. Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subject to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 2 mg to about 2 g, with from about 5 to about 360 mg being preferred. Expressed in proportions, the active compound is generally present in from about 2 to about 100 mg/ml of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered. Daily dosages up to about 5 to 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the host harboring the cancer. As used herein, cancer disease means blood malignancies such as leukemia, as well as other solid and non-solid malignancies such as the melanocarcinomas, lung carcinomas, and mammary tumors. By regression and palliation is meant arresting or retarding the growth of the tumor or other manifestation of the disease compared to the course of the disease in the absence of treatment.

This invention will be described in greater detail in conjunction with the following, non-limiting, specific examples.

EXAMPLE 1

[2,2-Bis(aminomethyl)-1,3-propanediol-N,N']dichloroplatinum

The compound 2,2-dibromomethyl-1,3-propanediol was prepared by the method of M. Saivier, et al, Can. J. Chem; 44, 1599 (1966).

A mixture of 13.1 g of 2,2-dibromomethyl-1,3-propanediol, 6.5 g of sodium azide and 750 ml of dimethylformamide was stirred and heated at 110°–120° C. for 20 hours, then clarified and the filtrate evaporated. The residue was extracted three times with dichloromethane. The extracts were combined and evaporated, giving 13.65 g of 2,2-bis(azidomethyl)-1,3-propanediol, compound with dimethylformamide.

A 13 g portion of the above azido derivative was reduced with 0.1 g of platinum dioxide in ethanol, using 50 lb. of hydrogen pressure for 20 hours. The mixture was then filtered and the filtrate concentrated to dryness, giving 9.34 g of 2,2-bis(aminomethyl)-1,3-propanediol as a pale yellow oil.

A mixture of 1.34 g of 2,2-bis(aminomethyl)-1,3-propanediol, 4.15 g of potassium dichloroplatinate and 22 ml of water was stirred for 2 hours, then cooled, the solid collected and washed three times with cold water. This solid was recrystallized from 60 ml of hot water, giving 890 mg of the desired product as beige crystals, mp 223°–225° C. (dec.).

EXAMPLE 2

Dichloro(tetrahydro-4H-pyran-4,4-dimethanamine-N,N')platinum

A mixture of 28.6 g of dichloroethyl ether, 13.2 g of malononitrile, 55.28 g of potassium carbonate and 800 ml of acetonitrile was refluxed on a steam bath for 24 hours, then filtered while hot. The filtrate was evaporated and the residue crystallized with charcoal treatment from 100 ml of ethanol, giving 9.5 g of tetrahydro-4H-pyran-4,4-dicarbonitrile as colorless plates, mp 110°–112° C.

A 180° ml portion of 1N borane in tetrahydrofuran was added rapidly, but dropwise, to a solution of 8.18 g of tetrahydro-4H-pyran-4,4-dicarbonitrile in 150 ml of tetrahydrofuran. This mixture was warmed, then cooled to room temperature in an ice bath and then stirred for 64 hours at room temperature. A 100 ml portion of ethanol was added dropwise, then the mixture was stirred for 4 hours and evaporated to dryness. The residue was taken up in 100 ml of water, acidified with 50 ml of 6N hydrochloric acid and extracted three times with ether. The remaining aqueous layer was evaporated to dryness. The residue was boiled in 300 ml of methanol and filtered while hot. The filtrate was treated with 200 ml of ether and cooled. The resulting solid was collected, washed with ether and dried, giving 8.31 g of tetrahydro-4H-pyran-4,4-dimethanamine, dihydrochloride, mp 258°–262° C. (dec.).

A mixture of 2.17 g of the above compound and 1.64 g of sodium acetate in 50 ml of water was treated with 4.15 g of potassium tetrachloroplatinate. The reaction was repeatedly filtered to remove successive crops of black to red crystals. When no more precipitates formed the mixture was allowed to stand overnight. The gold crystals were collected, giving 400 mg of the desired product, mp 280°–282° C. (dec.).

EXAMPLE 3

Dichloro(1,3-dioxane-5,5-dimethanamine-N,N')platinum

A suspension of 26.2 g of 2,2-bis(bromomethyl)-1,3-propanediol, 50 ml of concentrated hydrochloric acid and 50 ml of 38% formaldehyde was stirred in a 50° C. oil bath overnight, then cooled to room temperature and filtered. The filtrate was extracted with three 100 ml portions of ether. The ether extracts were combined, washed with water, dried and evaporated to an oil. A small amount of solid which formed was removed by filtration and washing with ether. The filtrate and wash were evaporated under reduced pressure, giving 26.9 g of 5,5-bis(bromomethyl)-1,3-dioxane as a clear oil.

A suspension of 2.69 g of 5,5-bis(bromomethyl)-1,3-dioxane, 3.8 g of sodium azide and 50 ml of dimethylformamide was heated at 130° C. in an oil bath overnight, then cooled and filtered. The filtrate was evaporated to an oily suspension which was diluted with 30 ml of water. The oily phase was extracted with three 25 ml portions of ether. The ether extracts were combined, dried and evaporated, giving 1.95 g of 5,5-bis(azidomethyl)-1,3-dioxane.

A mixture of 1.95 g of the 5,5-bis(azidomethyl)-1,3-dioxane, 0.5 g of 10% palladium on calcium carbonate and 40 ml of ethanol was reduced for 2 hours and then filtered. The filtrate was evaporated, giving 1.41 g of 1,3-dioxane-5,5-dimethanamine as an oil.

A 1.276 g portion of 1,3-dioxane-5,5-dimethanamine was dissolved in 5 ml of water and added to a solution of 3.62 g of potassium tetrachloroplatinate in 20 ml of water. The mixture was stirred overnight, then the solid was collected, washed with water, ethanol and ether and dried, giving 2.9 g of the desired compound.

EXAMPLE 4

Tetrahydro-4H-pyran-4,4-dicarboxylic acid, disilver (1+)salt

A mixture of 20.4 g of tetrahydro-4H-pyran-4,4-dicarbonitrile, 45 ml of 10N sodium hydroxide and 225 ml of ethanol in 105 ml of water was heated at reflux for 5 hours. Then the solution was evaporated to dryness. The residue was dissolved in 50 ml of water and the solution was adjusted to pH 1.5 with nitric acid. The solution was cooled in an ice bath then kept at room temperature for 16 hours. The crystallized product was collected by filtration, washed with water and dried to give 8.44 g of tetrahydro-4H-pyran-4,4-dicarboxylic acid as white crystals, mp 155° C. (dec.).

A 1.74 g amount of the preceding product was dissolved in 20 ml of 1N sodium hydroxide then one drop of a solution of 3.39 g of silver nitrate in 8.0 ml of water was added, followed by the dropwise addition of dilute nitric acid until the pH of the solution reached pH 11.9. The mixture was filtered to remove some precipitated solid, then the remaining silver nitrate solution was added to the filtrate with stirring and a thick white precipitate was formed. The mixture was stirred in the dark for several minutes then the solid was collected by filtration, washed with water and dried in vacuo to give 3.05 g of the desired product as a white solid.

EXAMPLE 5

[Tetrahydro-4H-pyran-4,4-dicarboxylato(2-)-O,O'](tetrahydro-4H-pyran-4,4-dimethanamine-N,N')platinum A suspension of 4.1 g of dichloro(tetrahydro-4H-pyran-4,4-dimethanamine-N,N')platinum and 3.88 g of tetrahydro-4H-pyran-4,4-dicarboxylic acid disilver salt in 400 ml of water was stirred in the dark for 16 hours. The solid was removed by filtration and the light yellow filtrate was evaporated to dryness under reduced pressure. The residue was slurried in water and heated at 95° C. in an oil bath for about 5 minutes. The mixture was filtered hot to collect 2.1 g of the desired product as colorless crystals.

EXAMPLE 6

Diammine[tetrahydro-4H-pyran-4,4-dicarboxylato(2-)-O,O']platinum

A suspension of 1.2 g of cis-diamminedichloroplatinum and 1.55 g of tetrahydro-4H-pyran-4,4-dicarboxylic acid disilver salt in 120 ml of water was stirred in the dark for 16 hours. The solid was removed by filtration and the filtrate was evaporated to about 5 ml. The colorless crystals that formed were collected, washed with water and dried to give 576 mg of the desired product.

EXAMPLE 7 trans-(−)-(1,2-Cyclohexanediamine-N,N')[tetrahydro-4H-pyran-4,4-dicarboxylato(2-)-O,O']platinum To a stirred solution of 9.12 g of (−)-R,R-1,2-diaminocyclohexane in 50 ml of water was added a solution of 33.2 g of potassium tetrachloroplatinate in 200 ml of water. Within a few minutes a yellow solid began to crystallize. The suspension was stirred at room temperature for 16 hours, then the solid was collected by filtration, washed with water and dried to give 29.63 g of trans-1,2-cyclohexanediamine, compound with platinum chloride (1:1).

A suspension of 1.9 g of the preceding compound and 1.94 g of tetrahydro-4H-pyran-4,4-dicarboxylic acid disilver salt in 190 ml of water was stirred in the dark for 16 hours. A white solid was removed by filtration and the filtrate was evaporated to dryness at reduced pressure to give 2.05 g of the desired product.

EXAMPLE 8

[2,2-Bis(aminomethyl)-1,3-propanediol-N,N'][tetrahydro-4H-pyran-4,4-dicarboxylato(2-)-O,O']platinum A suspension of 2.18 g of [2,2-bis(aminomethyl)-1,3-propanediol-N,N']dichloroplatinum and 2.11 g of tetrahydro-4H-pyran-4,4-dicarboxylic acid disilver salt in 220 ml of water was stirred in the dark for 16 hours. The solid remaining was filtered off and the filtrate was concentrated to about 50 ml. A small amount of amorphous solid which precipitated was removed by slow filtration. The filtrate was evaporated to dryness and the gummy residue was taken up in ethanol. The solid was collected by filtration, washed with ethanol and dried. The solid was recrystallized from water to give 1.48 g of the desired product as an amorphous solid.

EXAMPLE 9

(1,3-Dioxane-4,4-dimethanamine-N,N')[tetrahydro-4H-pyran-4,4-dicarboxylato(2-)-O,O']platinum A suspension of 2.06 g of dichloro(1,3-dioxane-5,5-dimethanamine-N,N')platinum and 1.94 g of tetrahydro-4H-pyran-4,4-dicarboxylic acid disilver salt in 190 ml of water was stirred in the dark for 16 hours. Then the mixture was filtered and the filtrate was evaporated to dryness to give 1.73 g of the desired product as a colorless solid.

What is claimed is:

1. A compound of the formula:

$$\begin{array}{c} A \\ \diagdown \\ A' \end{array} Pt \begin{array}{c} L \\ \diagup \\ L' \end{array}$$

wherein A and A' are both $NH_3$ or when taken together are:

(a) $R_1, R_2$ with two $-NH_2$ groups (b) $R_4, R_5$ with $-(CH_2)_n-NH_2$ and $-(CH_2)_{n'}-NH_2$ groups where $R_1$ and $R_2$ are the same or different and are hydrogen, $HO(CH_2)_m-$ where m is an integer from 1 to 3, or lower alkyl having from one to three carbon atoms and $R_1$ and $R_2$ taken together are $-(CH_2)_{m'}-B-(CH_2)_{m''}-$ where B is oxygen, $-SO_2-$, $-CH_2-$ or $N-R_3$ and $R_3$ is lower alkyl having from one to three carbon atoms and where m' and m'' are integers from 0–4 or

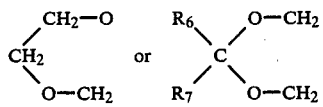

where $R_6$ and $R_7$ are hydrogen or lower alkyl having from one to three carbon atoms; wherein in formula (b) n and n' are either zero or one; $R_4$ and $R_5$ are $HO(CH_2)_m$— where m is an integer from 1 to 3, or $R_4$ and $R_5$ taken together are $(CH_2)_p$—D—$(CH_2)_p$—' where D is oxygen, —$CH_2$— or

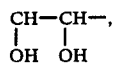

p and p' are integers from 0–4; $R_4$ and $R_5$ taken together are

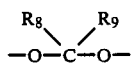

where $R_8$ and $R_9$ are hydrogen or lower alkyl having from one to three carbon atoms; and wherein L and L' taken together are a dibasic carboxylate of:

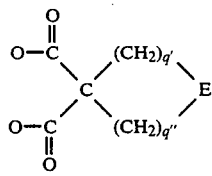

and E is oxygen, —$SO_2$— or N—$R_{10}$ where $R_{10}$ is lower alkyl having from one to three carbon atoms and q' and q'' are an integer from 0-4 or

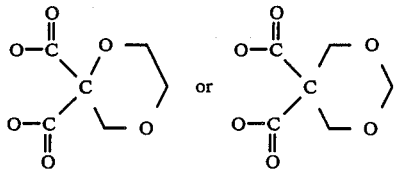

2. A compound according to claim 1, [tetrahydro-4H-pyran-4,4-dicarboxylato(2-)-O,O'](tetrahydro-4H-pyran-4,4-dimethanamine-N,N')platinum.

3. A compound according to claim 1, diammine[tetrahydro-4H-pyran-4,4-dicarboxylato-(2-)O,O']-platinum.

4. A compound according to claim 1, trans-(—)-(1,2-cyclohexanediamine-N,N')[tetrahydro-4H-pyran-4,4-dicarboxylato(2-)-O,O']platinum.

5. A compound according to claim 1, [2,2-bis-(aminomethyl)-1,3-propanediol-N,N'][tetrahydro-4H-pyran-4,4-dicarboxylato(2-)-O,O']platinum.

6. A compound according to claim 1, (1,3-dioxane-4,4-dimethanamine-N,N')[tetrahydro-4H-pyran-4,4-dicarboxylato(2-)-O,O']platinum.

7. A method of treating tumors sensitive to treatment with the compounds below in warm-blooded animals which comprises administering to the animals an oncolytic amount of a compound of claim 1.

8. A composition of matter in dosage unit form comprising from about 1 mg to about 1.2 g per square meter of mammalian body surface area of a compound of claim 1, in association with a pharmaceutically acceptable carrier.

* * * * *